United States Patent [19]
Dalos

[11] Patent Number: 5,427,947
[45] Date of Patent: Jun. 27, 1995

[54] ENVIRONMENTAL CHAMBER AND METHOD FOR COMPOSTING SOLID WASTE

[76] Inventor: David E. Dalos, R.R. #1, Box 307, Dent, Minn. 56528

[21] Appl. No.: 36,764

[22] Filed: Mar. 25, 1993

[51] Int. Cl.⁶ .............................................. C12M 1/10
[52] U.S. Cl. .................................. 435/312; 435/315; 435/316; 422/184; 422/209; 366/220; 366/225; 366/228; 366/233
[58] Field of Search ............... 435/287, 299, 300, 303, 435/312, 313, 315, 316; 422/184, 209; 366/220, 225, 228, 233, 135, 165, 187; 34/130, 138, 134; 71/8-10

[56] References Cited

U.S. PATENT DOCUMENTS

| | | | |
|---|---|---|---|
| 2,091,850 | 8/1937 | Gohre | 422/209 |
| 2,518,636 | 8/1950 | Phillips | 366/233 |
| 2,948,593 | 8/1960 | Larson | 422/209 |
| 2,994,592 | 8/1961 | Scovel et al. | 422/209 |
| 3,149,922 | 9/1964 | Lavallee | 422/209 |
| 3,171,723 | 3/1965 | Hansen | 422/209 |
| 3,245,759 | 4/1966 | Eweson | 435/312 |
| 3,676,074 | 7/1972 | Shibayama et al. | 422/209 |
| 3,765,102 | 10/1973 | Fischer | 34/136 |
| 3,847,803 | 11/1974 | Fisk . | |
| 4,127,388 | 11/1978 | Maczko et al. | 422/258 |
| 4,204,842 | 5/1980 | Morel et al. | 435/167 |
| 4,252,901 | 2/1981 | Fischer et al. | 210/603 |
| 4,255,389 | 3/1981 | Jung et al. | 422/209 |
| 4,272,489 | 6/1981 | Lutz et al. | 422/209 |
| 4,372,856 | 2/1983 | Morrison | 210/603 |
| 4,487,510 | 12/1984 | Buurman et al. | 366/337 |
| 4,511,370 | 4/1985 | Hunziker et al. | 210/603 |
| 4,514,297 | 4/1985 | Enqvist | 210/603 |
| 4,565,552 | 1/1986 | Cotton | 71/9 |
| 4,758,344 | 7/1988 | Wildenauer | 210/603 |
| 4,780,415 | 10/1988 | Ducellier et al. | 435/166 |
| 5,049,486 | 9/1991 | Blackwood et al. | 435/3 |
| 5,271,163 | 12/1993 | Pikus et al. | 34/33 |

FOREIGN PATENT DOCUMENTS

| | | | |
|---|---|---|---|
| 0109662 | 3/1900 | Germany | 422/209 |
| 0029468 | 3/1980 | Japan | 435/312 |

*Primary Examiner*—William H. Beisner
*Attorney, Agent, or Firm*—Haugen and Nikolai

[57] ABSTRACT

A rotatable environmental chamber for reducing solid waste includes a cylindrical container having front and rear end caps, seal bearings and support plates for journaling the container each having a central opening. The seal bearings are pinned to the end caps and fit into counterbores in the support plates. Pipes in communication with the inside of the container are connected to holes in the front end cap and seal bearing. Holes in the front support plate are aligned with recessed areas in the seal bearing. Liquids and/or a gas can be introduced through the front support plate and seal bearing to the container through the pipes as the container rotates. Variable pitch vanes inside the container are used to mix and direct the flow of waste. Isolation valves are used to seal the container. The environmental chamber may be used in a process for anaerobic and aerobic decomposition of organic materials and for reducing plastic and metals to other compounds.

22 Claims, 11 Drawing Sheets

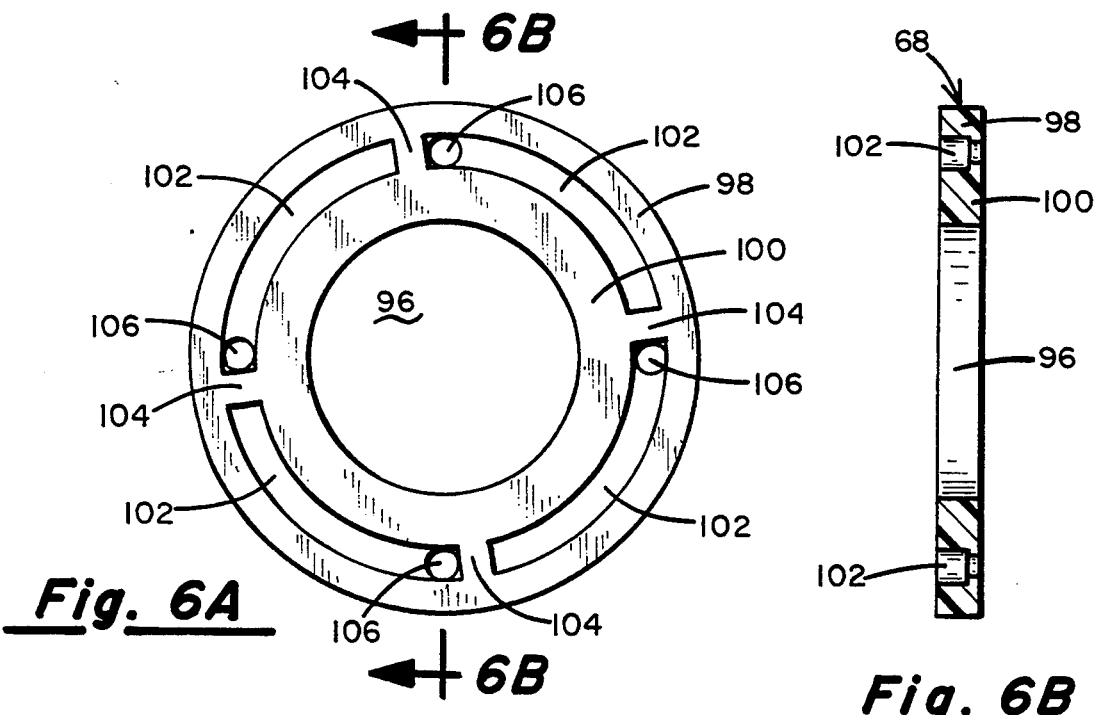
Fig. 6A
Fig. 6B
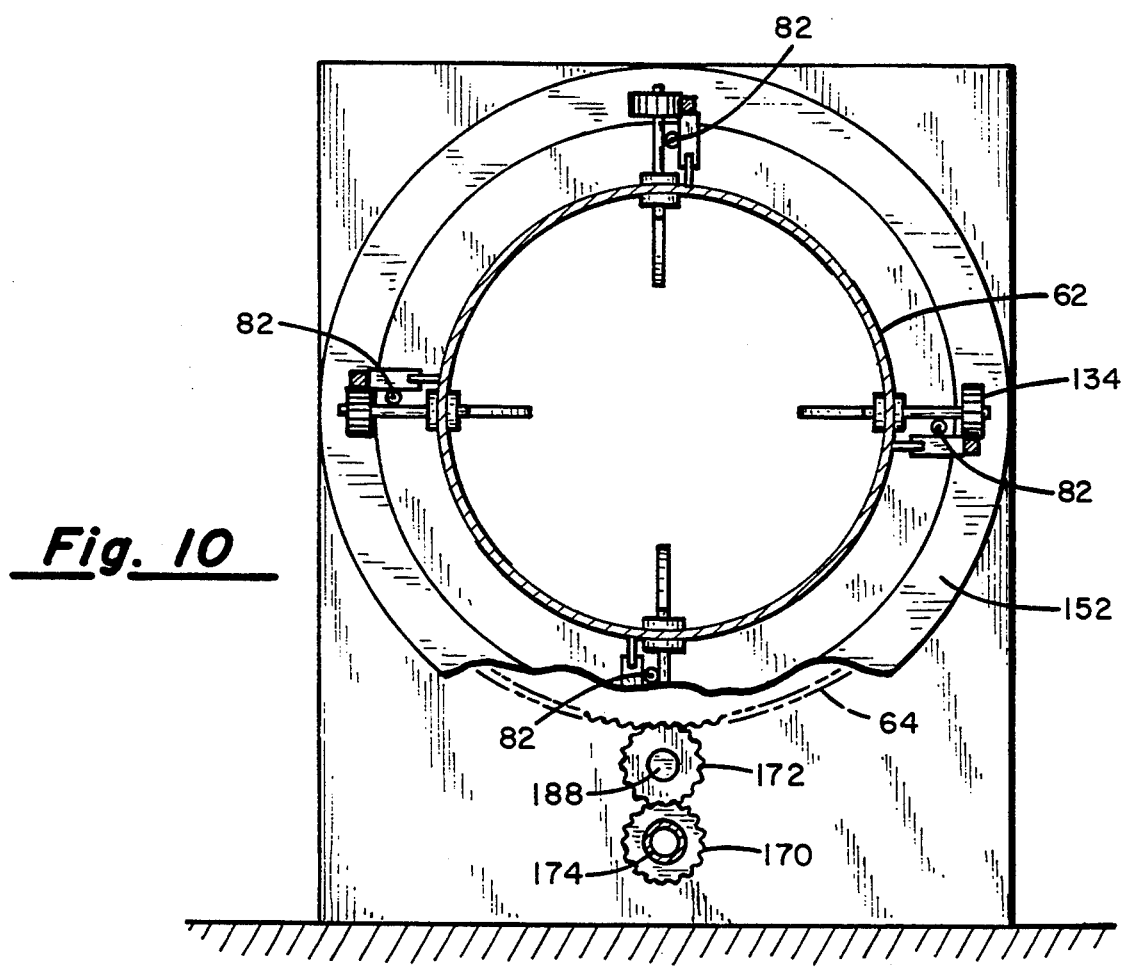
Fig. 10

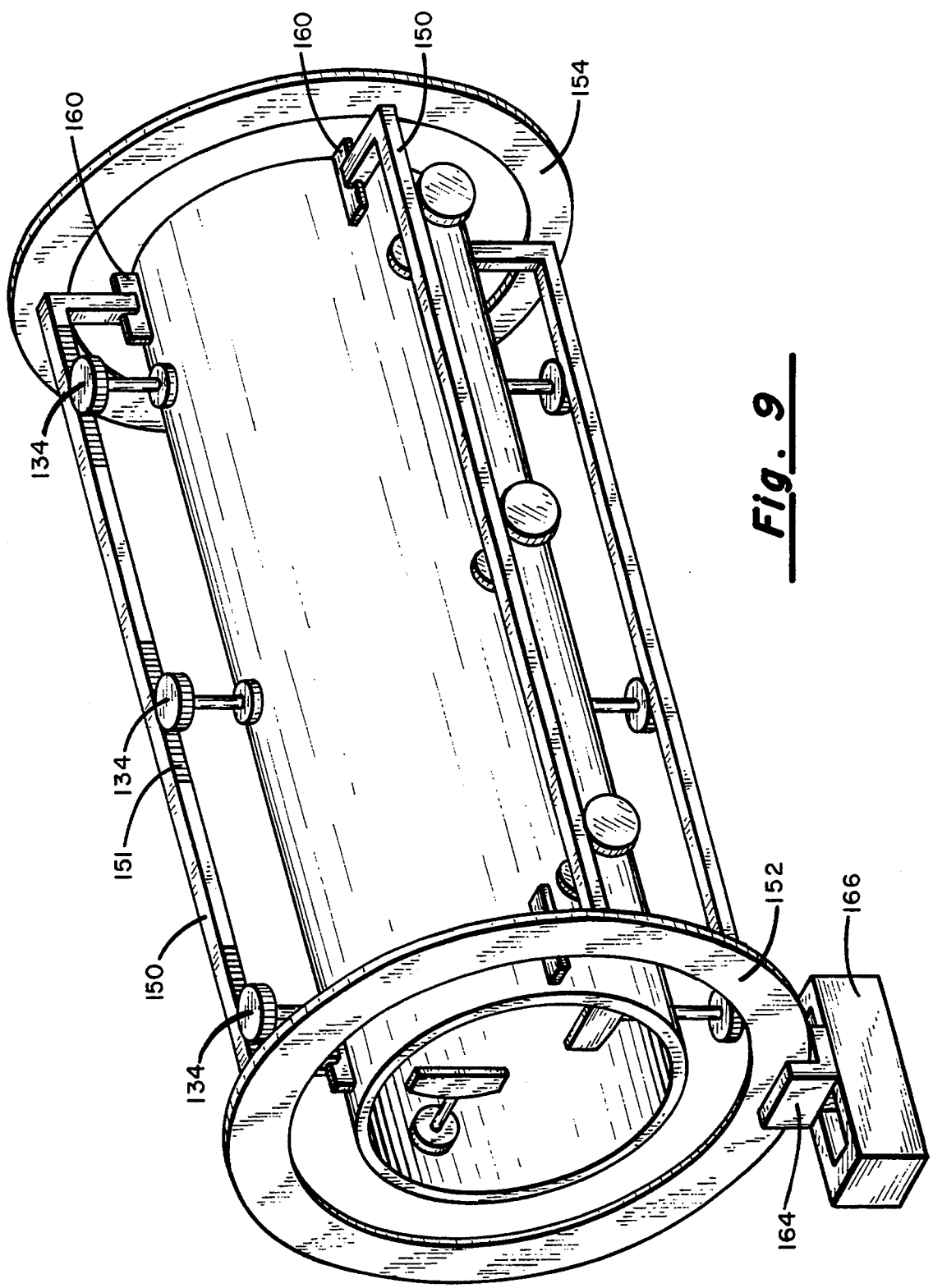

ENVIRONMENTAL CHAMBER AND METHOD FOR COMPOSTING SOLID WASTE

BACKGROUND OF THE INVENTION

I. Field of the Invention

This invention relates generally to waste reduction systems and more particularly to an improvement in an environmental chamber and a method of using same for composting and reducing solid waste.

II. Discussion of the Prior Art

Solid waste disposal has become a problem in many developed countries of the world. Existing landfills are reaching maximum capacity, and people oppose building new facilities due to pest and health hazards. Landfills contribute pollution to the surrounding land, air, and water. Leakage from the decomposing waste in the landfills enters the ground and adds toxic chemicals to the water table. If the landfill is close to the sea, run-off adds toxic chemicals to the ocean. Gases, such as methane and carbon dioxide, produced by decomposing waste are released into the atmosphere, contributing to the greenhouse effect. An alternative to landfills is needed to alleviate these problems.

Alternatives for decreasing reliance on landfills include burning the organic and inorganic waste for energy or composting the organic waste for fertilizer and recycling the inorganic waste. Producing energy by burning solid waste is also an attractive method. However, plastics are part of the waste, and when burned plastics release known carcinogens such as dioxin and chlorine. Although exhaust gases are scrubbed to remove toxins, the possibility of releasing them into the atmosphere still exists. A more cost-effective method of dealing with plastic waste is recycling.

Biodegrading organic waste produces material for supplementing soil fertilizer. During the decomposition process, typically methane, water vapor and carbon dioxide are released. These gases are usually released directly into the atmosphere. Instead, the methane and carbon dioxide should be trapped for later use or resale. The solid waste decomposition process is slow, taking several weeks before a final product is ready. To trap gases and speed up the biodegrading process, a closed loop environmental chamber can be used. In accordance with the present invention, a closed loop environmental chamber is configured to attain optimum conditions for decomposition. Plastic and other inorganic waste not broken down in the closed loop chamber are separated from the organic waste, reduced and sent to recycling centers for processing.

Systems for composting and separating organic waste from inorganic waste have been developed in the past. One process, described in U.S. Pat. No. 3,847,803, issued to Fisk, describes grinding the unsorted waste, treating the waste anaerobically to soften the biodegradable portion, separating the waste into biodegradable and non-biodegradable waste, treating the biodegradable waste aerobically in the presence of potassium and phosphorus, and curing the aerobically treated waste.

In the Fisk patent, the unsorted waste is treated anaerobically in one of three anaerobic predigestion tanks. The waste is held in the anaerobic predigestion tank for approximately three days. The tanks do not appear to thoroughly mix the solid waste or trap gases, such as methane, for later use. Instead, the Fisk patent warns that the dwell time of the waste in the anaerobic predigestion tanks should not extend beyond eight days, or methane gas will be produced. Thus, the process described in the Fisk patent does not accommodate the production of methane.

Fisk teaches that partially anaerobically decomposed waste be fed into a separation tank to separate the biodegradable waste from metal, glass, plastic, sand, grit, and other inorganic material. In the separation tank, fermentation causes the biodegradable waste to rise to the surface while the non-biodegradable waste settles to the bottom. The separation tank is not enclosed. Therefore, the gases and smells produced by the fermenting biodegradable waste are carried by the wind to neighboring communities.

In accordance with the Fisk patent, raw sewage is pumped into collecting tanks where enzymes are added. The Ph and temperature are regulated in the tanks to stimulate growth of aerobic bacteria for deodorizing the sewage. These tanks are enclosed cylinders. The treated raw sewage is thoroughly mixed with biodegradables taken from the separation tank. The resulting slurry is dewatered and transferred into the first of a series of three aerobic digestors, each having a one-day cycle.

The aerobic digestors are approximately 10 feet in diameter by 30 feet in height, having a spiral mixing auger installed vertically and extending almost the entire length of the tanks. The mixing auger is enclosed in an inner tube and conveys waste from the lower portion of the tank to the top. This agitation turns the biodegradable waste, allowing fungi to grow during the rest periods. The turned waste is subjected to gases that assist in decomposition and add value to the end product. Finally, the resultant material is transferred to a curing area where bacteria is sprayed on the finished product to add nitrogen and plant growth factor.

The process described in the Fisk patent does not trap carbon dioxide or methane. Gases produced during the fermentation process are released directly into the atmosphere. Metal and plastic are recovered using various sifters, but no reduction of the plastic or metal is described.

The present invention provides a method and a closed loop environmental chamber for trapping and extracting methane, carbon dioxide and other gases released during decomposition of the biodegradable waste or, in the alternative, ethanol as a fermentation byproduct. The method and environmental chamber of the present invention are also used for reducing plastic and metal to basic components for later reclamation.

Systems for producing and trapping methane are present in the prior art. U.S. Pat. No. 4,252,901, issued to Fischer et al., and U.S. Pat. No. 4,511,370, issued to Hunziker et al., each disclose a process for anaerobic decomposition of biodegradable waste to produce methane, carbon dioxide and a residual sludge material. However, neither of the patents disclose separating and reducing plastic or metal.

Methods for converting biodegradable waste and recovering gases usually use a series of tanks, often partially embedded in the ground, to hold the solid waste slurry. These tanks almost always have some means of agitating or mixing the slurry to achieve a uniform temperature and distribute the bacteria and chemicals used to promote decomposition. One method employed for agitating or stirring the solid waste slurry is rotating a horizontal rotary disk in a vertical tank. Another method employed is to introduce biogas to create a pneumatic thrust that causes a flow in the solid waste slurry.

U.S. Pat. No. 4,514,297, issued to Enqvist, describes a reactor for the anaerobic decomposition of organic sludge and the production of methane. The reactor comprises an essentially horizontal cylinder having an agitator rotating around a central horizontal shaft. At the top of one end of the reactor is an inlet port for introducing sludge, and at the top of the other end is an outlet port for discharging digested waste. Outlets for recovering methane are in the upper portion of the reactor.

The amount of sludge introduced at the inlet port and returned from the outlet determines the rate of flow through the reactor. The level of the sludge must be maintained above the central horizontal shaft to achieve flow. To maintain the desired level, the sludge presented at the inlet port must be externally regulated. Mixing blades on the agitator for moving the sludge from the middle or bottom of the reactor to the top do not regulate the rate of flow of sludge through the reactor.

The present invention provides an environmental chamber comprising a rotatable cylindrical container having directional vanes disposed inside the container. The pitch of the directional vanes can be changed from outside the container. The rate of flow of sludge through the chamber is regulated by the speed of rotation of the container and the pitch of the directional vanes. Fluids, gases and solid waste are introduced or discharged from the chamber through a plastic seal bearing, while the chamber rotates. The plastic seal bearing may be made from a high strength, resilient, synthetic material, such as nylon or a waxy material such as that sold by E. I. Du Pont De Nemours and Company under the trademark TEFLON®. Methane carbon dioxide, ethanol and other fermentation gases and fluids are trapped for later use or resale. The present invention allows for independent regulation of the rate of flow of sludge through the chamber and uses only one type of environmental chamber for organic decomposition and reducing metal and plastic to basic components.

From the above analysis, it can be seen that the prior art references of which I am aware, individually and as a whole, do not disclose a method for reducing solid waste using one type of environmental chamber for aerobic decomposition, anaerobic decomposition, reducing plastic, and reducing metal, or an environmental chamber that provides for independent regulation of the rate of flow of waste through the chamber.

SUMMARY OF THE INVENTION

It is accordingly a principal object of the invention to provide an improved method for decomposing and reducing solid waste.

Another object of the invention is to provide an improved method for decomposing and reducing solid waste using a single type of environmental chamber.

Yet another object of the invention is to provide an improved environmental chamber for the decomposition and reduction of solid waste.

Yet another object of the invention is to provide an improved environmental chamber for aerobic decomposition, anaerobic decomposition, reduction of plastic and reduction of metal.

Yet another object of the invention is to provide a rotatable environmental chamber having directional vanes disposed inside the environmental chamber for improved mixing and movement of the waste being processed.

Yet another object of the invention is to provide a rotatable environmental chamber having directional vanes disposed inside the chamber wherein the rate of flow of waste through the chamber is regulated by changing the pitch of the directional vanes and the speed of rotation of the environmental chamber.

The foregoing objects of the present invention are attained by providing a process for reducing solid waste, that may include human waste for treatment, comprising the steps of: (1) preparing the waste for shredding; (2) shredding the waste; (3) preparing the waste for anaerobic decomposition; (4) decomposing the waste anaerobically; (5) preparing the waste for aerobic decomposition; (6) decomposing the waste aerobically; (7) separating the inorganic waste from the organic waste; (8) reducing the plastic with solvents; and (9) reducing the metal with acids.

The steps of anaerobic decomposition (4), aerobic decomposition (6), reducing the plastic with solvents (8), and reducing the metal with acids (9) are performed in an environmental chamber. Each of the steps is carried out at a different temperature with different fluids, gases and chemicals added, including water, solvents, acids, $N_2$, $CO_2$ and Ph balancing chemicals.

After the solid waste is sorted and shredded, it is transferred to an environmental chamber where the Ph is balanced, air is purged with nitrogen and anaerobic bacteria is added for anaerobic decomposition. The temperature and moisture content are controlled to enhance decomposition. After anaerobic decomposition is complete the waste is discharged from the anaerobic decomposition chamber to an aerobic decomposition chamber. Aerobic bacteria is added with air at a controlled temperature for enhanced aerobic decomposition. Following aerobic decomposition, the anaerobically and aerobically decomposed waste is discharged from the aerobic decomposition chamber for separation from inorganic waste. The inorganic waste is separated from the organic waste with sifters. The plastic and metal removed from the partially treated mass are reduced in a series of environmental chambers using various solvents and acids.

The environmental chamber for carrying out the above process comprises a cylindrical container having front and rear end caps, support plates, and seal bearings. The end caps are welded to the ends of the cylindrical container. The seal bearings discs, are pinned to the end caps and fit into counterbores in the front and rear support plates. The seal bearings are preferably made from a high strength, resilient, plastic material, such as nylon or a waxy material such as that sold by E. I. DuPont De Nemours and Company under the trademark TEFLON®. The seal bearings act as lubricous bearings for rotating the container about its horizontal axis between the support plates. The end caps, support plates, and seal bearings each have central holes for permitting waste to flow through. The diameters of the central holes are all essentially the same.

Attached to the exterior of the container are four pipes. The pipes extend from the front to the rear of the container and are in fluid communication with the inside of the container. The four pipes pass through holes or bores formed in the front end cap and the front seal bearing. The holes, or bores, in the front seal bearing are in separate arcuate channels or recesses in the seal bearing. The recesses face the front support plate and are aligned with two holes in the front support plate. The holes in the front support plate are therefore in fluid communication through the recesses with the four pipes and the interior of the chamber. As explained below, using this seal bearing configuration, fluids and gases can be introduced and taken out of the environmental chamber while it rotates.

In particular, the front seal bearing has an outer rim and an inner rim facing the front support plate. Between the outer and inner rims is a recessed area. The recessed area is divided into four distinct arcuate channels by wall members, each channel having one hole or bore communicating therewith. One of the two holes in the front support plate is in fluid communication with one of the channels or recessed areas and the inside of the cylindrical container through a first pipe and the other hole in the front support plate is in independent and exclusive fluid communication with a different arcuate channel or recessed area and a second pipe. Fluids, such as water, ethanol or steam, and gases, such as Air, $N_2$ or Methane, can be separately injected or taken out of the environmental chamber through the holes in the support plates while the chamber rotates.

The front and rear end caps are circular in shape and have gear teeth along their outer diameter. Rotation is achieved by meshing the teeth along the outer diameter of the end caps with gear assemblies external to the chamber. A motor rotates the gear assemblies and the cylindrical container.

Disposed inside the cylindrical container are a plurality of sets of directional vanes, e.g., three sets. Each set has four vanes spaced at 90° intervals around the circumference of the cylindrical container. Each vane is somewhat semicircular in shape, having one side that fits the contour of the wall of the container and another side that is straight. The straight sides of the vanes do not interfere with each other. The three sets of directional vanes are longitudinally separated from one another within the chamber. One set is in the front, one set is in the rear and a third set is in the middle.

Each of the 12 vanes is connected to a shaft extending through the wall of the container. Connected on the outside of the container to each of the shafts is a gear. Rotation of the gear changes the pitch of the associated vane. Three directional vanes, one from each set, are horizontally aligned, parallel to the rotational axis of the cylindrical container. Four directional vane gear bars are operatively connected to the four sets of three horizontally aligned vanes and to circular front and rear directional vane gear rings. The circular directional vane gear rings are slidably attached to the cylindrical container. The front directional vane gear ring has an outer rim of larger diameter in contact with prongs of a directional fork assembly. The directional fork assembly is attached to earth and moves left or right, moving the directional vane gear rings and the directional vane gear bars left or right. The engagement of the gear bars with the gears connected to the vanes causes the pitch of the directional vanes to change. By altering the pitch of the directional vanes, the waste in the environmental chamber can be mixed more or less thoroughly. Further, by altering the pitch of the directional vanes and increasing the rate of rotation of the chamber, the waste can be discharged at will.

Attached to the outside surfaces of the front and rear support plates are isolation valves for sealing the environmental chamber shut during the decomposition and reduction steps. The front input side isolation valve and the rear output side isolation valve are essentially the same. An isolation valve is a rectangular box having a central hole through its major surfaces. The central hole aligns with the central holes in the support plates, seal bearings and end caps of the container. Disposed inside the isolation valve is a rectangular valve plate having two major surface areas and a circular O-ring seal on one major surface area. The diameter of the O-ring seal is slightly larger than the central hole of the isolation valve. To seal the container, an air driven cylinder forces the valve plate down. The bottom of the valve plate and the bottom of the inside of the isolation valve are angled to force the valve plate securely against the inside of the isolation valve. The O-ring seal forms a seal around the central hole in the valve, sealing the container shut.

A movable bin and auger is used to transfer waste into the environmental chamber. The bin collects waste falling from above and the auger, connected to the base of the bin, transfers the waste into the environmental chamber. The entire bin and auger arrangement is slidably attached to an in-out drive assembly for moving the mouth of the auger into and away from the central hole of the front support plate of the environmental chamber. To remove waste from the environmental chamber, a trough and auger are moved into the central hole of the rear support plate. The waste removed by the auger is transferred to an attached drop chute and dropped into an awaiting input bin.

In operation, the bin at the front of the environmental chamber is loaded with waste and the front isolation valve plate is lifted to open the environmental chamber. The bin and auger are moved forward by the in-out drive assembly until the mouth of the auger is inside the central opening of the environmental chamber's front support plate. The auger is turned on and the waste is transferred into the environmental chamber. The rear isolation valve remains closed during this process. When loading is complete, the front bin and auger are moved away from the front isolation valve and the valve plate is forced down to seal the container shut. Decomposition or reduction takes place inside the rotating chamber. After the desired process is complete, the rear isolation valve is opened and the trough and rear auger are moved inside the central opening of the rear support plate. Rotating the container and altering the pitch of the directional vanes discharges the waste into the trough and rear auger. The auger carries the waste away from the output of the environmental chamber and dumps the waste into an awaiting input bin beneath the drop chute. After unloading is complete, the trough, rear auger and drop chute are moved away from the environmental chamber, the rear isolation valve is closed and the front isolation valve is opened to repeat the process. This procedure is repeated from one chamber to another until the steps of the process for decomposing and reducing waste are completed.

Other objects, features and advantages of the present invention will become apparent to those skilled in the art through the description of the preferred embodiment, claims and drawings herein.

BRIEF DESCRIPTION OF THE DRAWINGS

FIG. 6A is an end view of the seal ring used in the preferred embodiment of FIG. 4;

FIG. 6B is a cross-sectional view taken along line 6B—6B in FIG. 6A;

FIG. 9 is a perspective view illustrating the mechanism for setting the angular position of all directional vanes in the plural sets simultaneously;

FIG. 10 is a view showing the drive assembly for the environmental chamber;

DESCRIPTION OF THE PREFERRED EMBODIMENT

Figure 1:
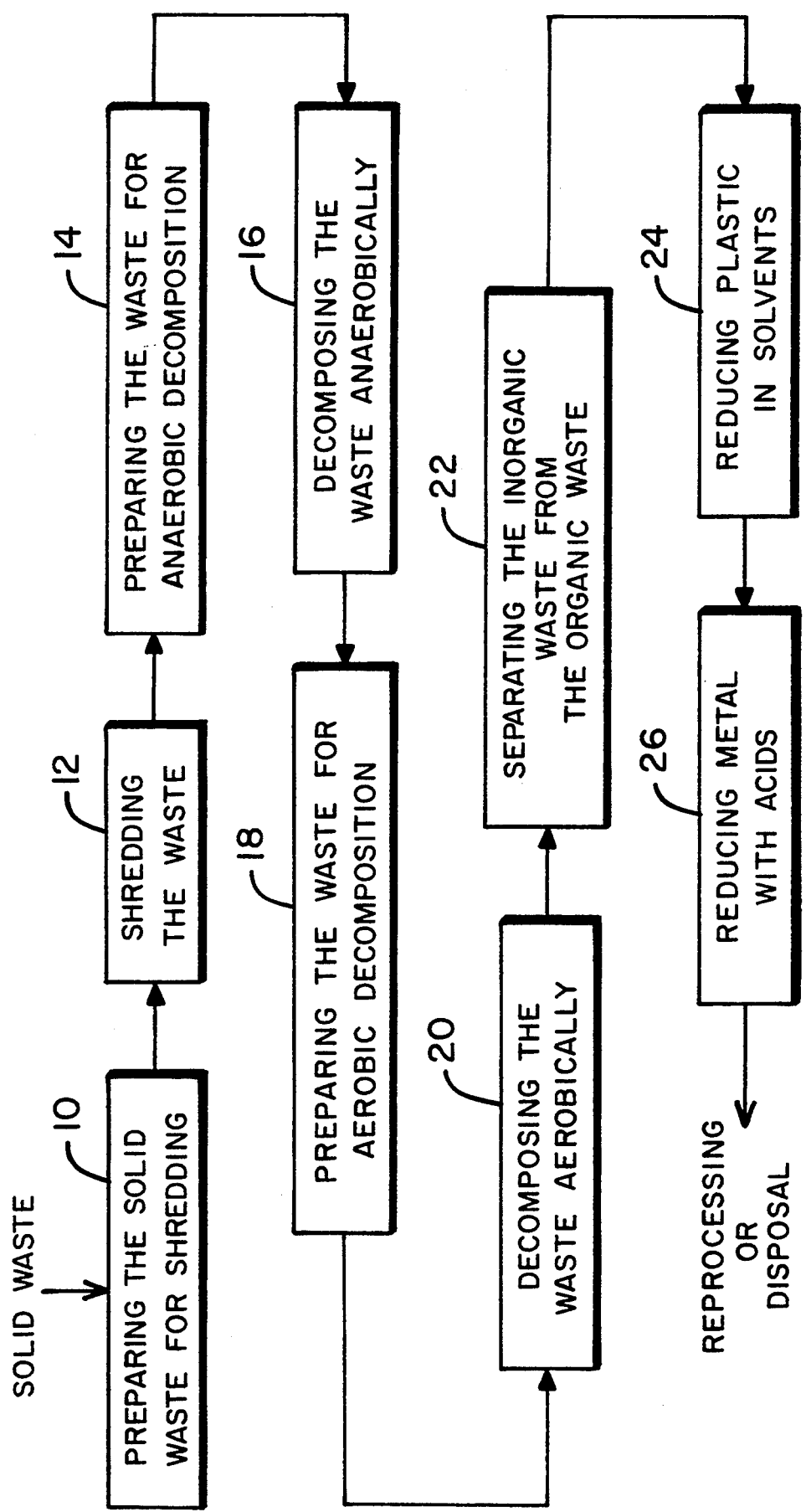
FIG. 1 is a flow diagram illustrating the process steps carried out in accordance with the present invention.

FIG. 1 is a process flow diagram showing the steps for reducing solid waste. The steps include: (a) preparing the solid waste for shredding 10; (b) shredding the waste 12; (c) preparing the waste for anaerobic decomposition 14; (d) decomposing the waste anaerobically 16; (e) preparing the waste for aerobic decomposition 18; (f) decomposing the waste aerobically 20; (g) separating the inorganic waste from the organic waste 22; (h) reducing the plastic with solvents 24; and (i) reducing the metal with acids 26. The anaerobic and aerobic decomposition steps (16 and 20) and the plastic and metal reduction steps (24 and 26) are performed in the environmental chamber 60, FIG. 4. In general, the environmental chamber 60 provides a closed system for controlling an environment to accomplish efficient decomposition and reduction of solid waste. Solid waste, including human waste if present, is loaded into the chamber, mixed with chemicals and gases, and heated to the correct temperature for enhancing decomposition or reduction of the waste. The chamber 60 is used to biodegrade organic waste such as human waste to methane and/or ethanol, and fertilizer, and to reduce plastic and metal to basic components. Although the solid waste differs in its chemical and physical make up, it is all processed in the same basic type of chamber. The major differences in the steps employed are the type of waste being processed, the temperature at which it is processed and the chemicals and gases added for decomposing or reducing it. The environmental chamber 60 is used to control all parameters of the process. Temperature, relative humidity, barometric pressure, pH value, motion, and direction of flow of the waste are each controlled by the environmental chamber. Gas and fluid produced by the decomposition of organic waste is trapped by the system, removed from the chamber 60 and either used in the solid waste reduction process, used to create electricity, or sold.

Figure 2:
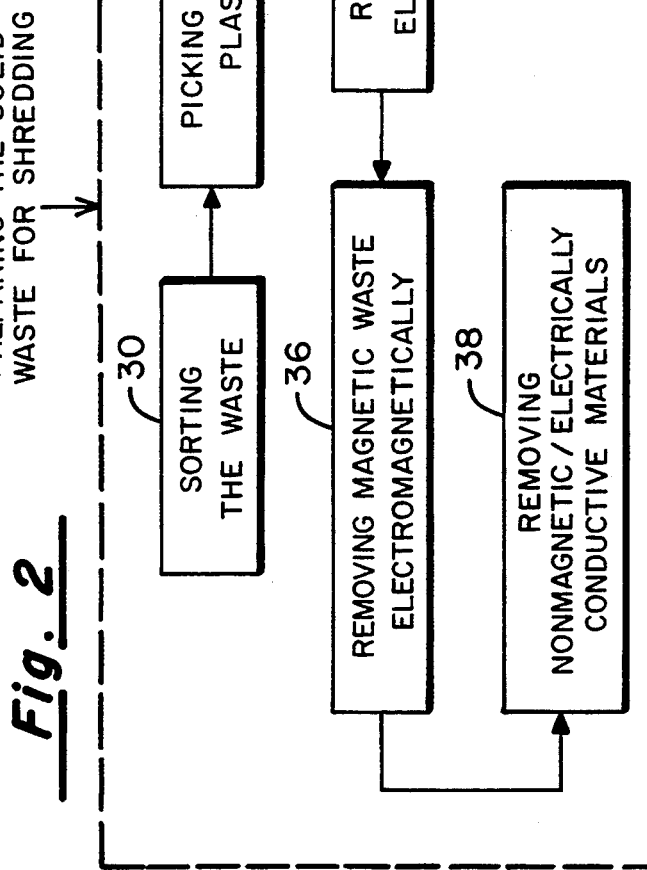
FIG. 2 is a further flow diagram illustrating in greater detail the steps employed in preparing waste for processing.

The first step in the reduction process is preparing the solid waste for shredding 10. Only properly sized waste is loaded into an environmental chamber 60 for processing. As shown in FIG. 2, preparing the solid waste for shredding 10 comprises the steps of: (a) sorting the waste 30 to get rid of unfavorable articles such as rock, cement, etc.; (b) picking and ripping plastic bags 32; (c) removing plastic electrostatically 34; (d) removing magnetic waste electromagnetically 36; and (e) removing non-magnetic/electrically conductive materials 38 with arc welding techniques.

Sorting the waste 30 involves inspecting the waste for toxic and hazardous material such as batteries, gas tanks, explosives, and pesticides. The waste is further inspected for over-sized items that could not be shredded by the shredding equipment. The remaining waste is transferred to step 32 for picking and ripping plastic bags. At this step, plastic bags containing garbage are picked up and ripped open, exposing the contents of the bags. The plastic bags are removed for reducing at a later time and the remaining waste is transferred to the step for removing plastic electrostatically 34. Here, plastic that will receive an electrostatic charge is lifted from the waste. The waste is next transferred to the step for removing magnetic materials electromagnetically 36. Here, an electromagnet is energized to remove waste capable of being polarized and picked up with a magnet. Next, the waste is transferred to the step for removing non-magnetic/electrically conductive material 38. Using arc welding techniques, materials such as aluminum are picked out of the waste. The remaining waste is ready for feeding into a shredder. The shredder chops the waste to the proper size for loading into an environmental chamber 60.

Figure 3:
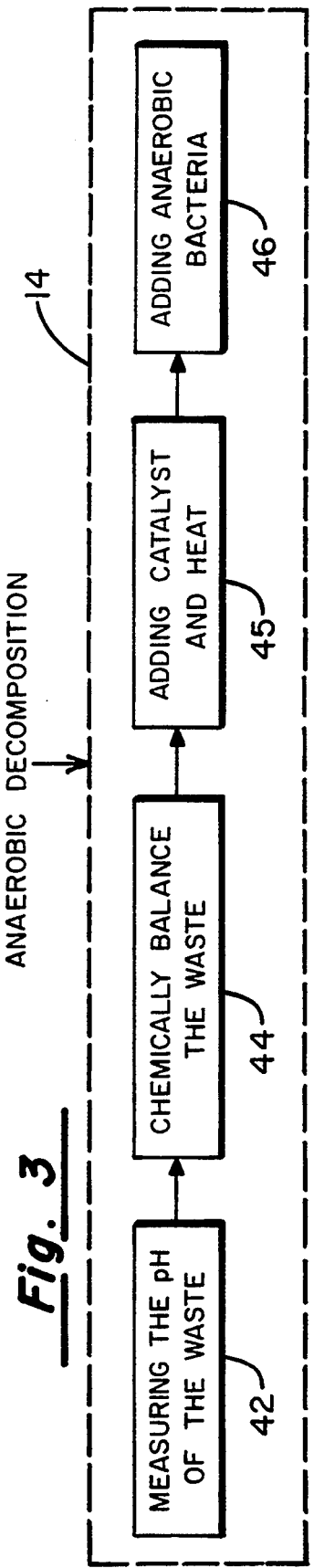
FIG. 3 is still a further process flow diagram illustrating the steps for preparing the waste for anaerobic decomposition.

After shredding, the waste is transferred into an environmental chamber 60 to be prepared for anaerobic decomposition 14. As shown in the flow diagram of FIG. 3, the process of preparing the waste for anaerobic decomposition 14 comprises: (a) measuring the pH of the waste 42; (b) adding acids and bases as needed to chemically balance the waste 44; (c) adding a catalyst and heat 45 for stimulating growth of bacteria and aiding in decomposition; and (d) adding anaerobic bacteria 46. The pH of the waste is measured using standard industry techniques. Next, chemicals such as lime (base) and dilute HCl (acid) are added for balancing the pH. Heated nitrogen is then added to ensure an ideal growth medium for the bacteria. The heated nitrogen purges the air from the environmental chamber 60. Next, methane producing or methanogenic bacteria from the orders methanobacteriales, methanococcaceae, and methanomicrobiales are added to produce methane from the organic waste. Other methane producing bacteria genetically engineered to maximize methane production may also be used. In the alternative, ethanol producing bacteria such as Escherichia coli, as described in U.S. Pat. No. 5,000,000, issued to Ingram et al., may be employed during anaerobic decomposition 14 to produce ethanol from the waste. The nitrogen and methane gas or ethanol is removed from the chamber and separated. The nitrogen is reheated and reused and the methane is liquified. The methane or ethanol is either used for energy production or sold. Once the anaerobic bacteria have completed their activity, the waste is discharged to the next environmental chamber 60 for aerobic decomposition.

The waste is prepared for aerobic decomposition (step 18) by balancing the pH, adding heated air and aerobic bacteria. The aerobic bacteria added may be an Escherichia coli which has been transformed into an ethanol producing bacteria as in the Ingram et al. patent. The same pH correcting chemicals used in anaerobic decomposition, along with water, are added to ensure an optimum growth medium for the bacteria. As air is brought into the system, the mass is heated with hot air to the optimum temperature for bacteria growth. By-product gases such as water vapor and carbon dioxide are reduced. Water vapor is reduced to water and the heat is used to supplement the environmental chamber 60 heating requirements. The carbon dioxide is captured to be sold and ethanol is captured and used for energy production or sale. Once aerobic bacteria activity has slowed to a desired level, the waste is discharged from the environmental chamber 60 for separation.

Separating the inorganic waste from the organic waste 22 is accomplished by sending the anaerobically and aerobically decomposed waste through a plurality of vibration-grating machines. The unprocessed inorganic waste is separated from the processed organic waste. The inorganic waste is transferred to the next step for reducing the plastic with solvents 24.

At this step, one or a series of environmental chambers 60 are used with solvents to reduce various plastics to their basic components. Solvents used include acetone, alcohol, xylene, and hexane, depending on the plastic being reduced. To reduce the plastic, the waste is immersed in the solvent and heated to the boiling point of the solvent. The plastic being recovered decomposes in the chamber and the gases given off are reheated and reused for heating the chamber. The solvent, with dissolved plastic in it, is drained and sent to an evaporator to recover the solvent and the dissolved plastic.

After the plastics have been removed, the remaining inorganic waste is transferred to an environmental chamber 60 for reducing the metal with acids 26. Acids typically used in industry for reducing metals are used, leaving the metal in its native chemical state. Hydrogen and oxygen given off during the process are trapped for power generation or sale. This completes the decomposition and reduction of solid waste process. Remaining waste is reprocessed or disposed of in landfills. Glass and ceramic materials that are part of the original waste material are ground to a fine sand along with the organically decomposed waste for fertilizer.

Figure 4:
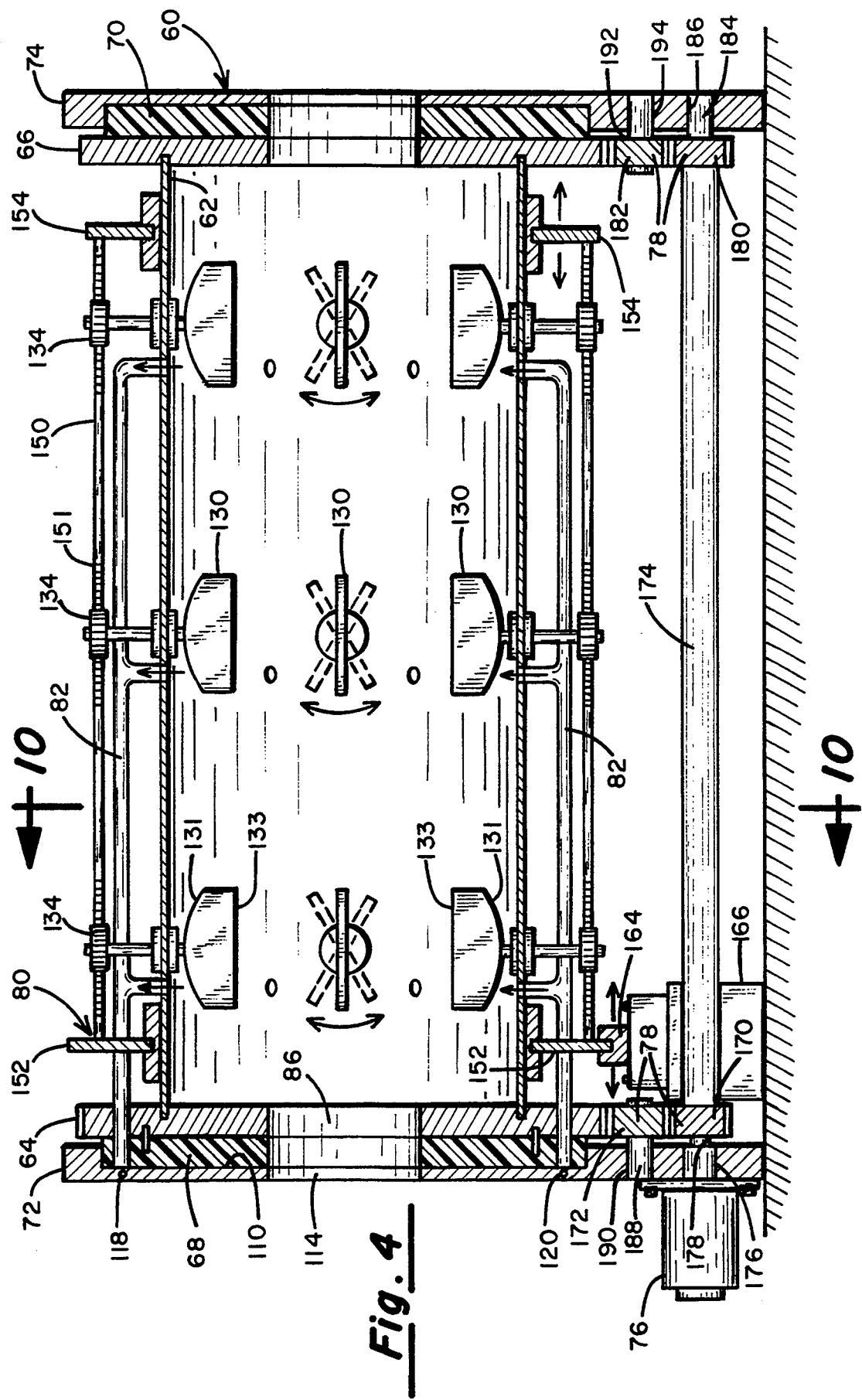
FIG. 4 is a longitudinal cross-sectional view of the environmental chamber in accordance with the preferred embodiment of the present invention.

Indicated generally in FIG. 4 is an environmental chamber 60 of the type used throughout this process for decomposing and reducing solid waste. The environmental chamber 60 comprises a hollow cylindrical container 62 having front and rear end caps 64 and 66, front and rear seal bearings 68 and 70, front and rear support plates 72 and 74, a motor 76 and gear assemblies 78 for rotating the cylindrical container 62, and means for mixing and directing the flow of waste, indicated generally by the numeral 80.

The cylindrical container 62, front and rear end caps 64 and 66, and front and rear support plates 72 and 74 are preferably made out of steel. The inside of the cylindrical container has either a coating of polyurethane or another tough, abrasion resistant plastic on it to prevent wear and erosion of the metal chamber surface.

Figure 5:
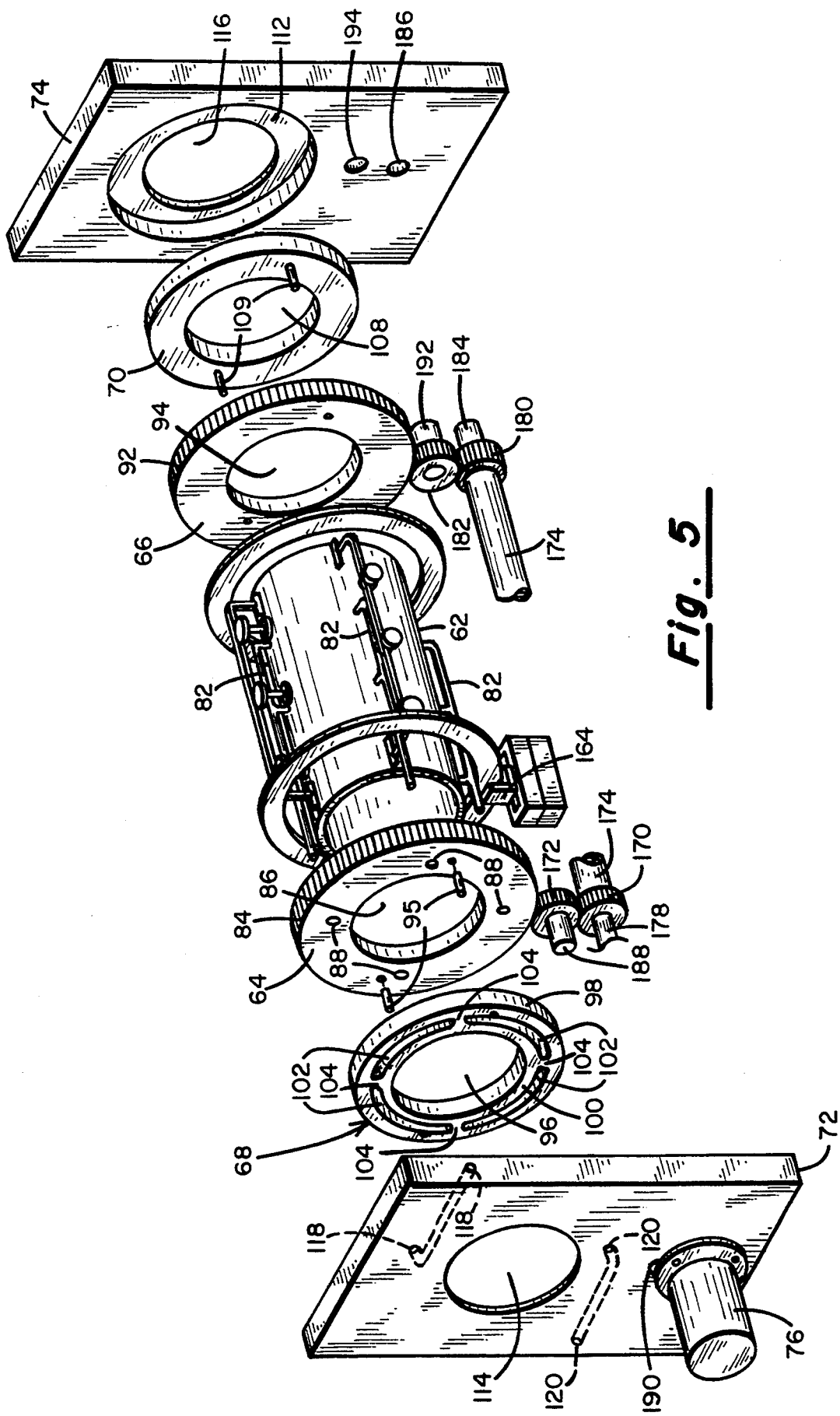
FIG. 5 is an exploded view showing the relationship of the parts comprising the environmental chamber of FIG. 4.

As indicated in FIGS. 4, 5 and 10, four pipes 82, made out of either steel or PVC, are mounted to the outside of the cylindrical container 62. Each pipe 82 is coupled into the cylindrical container 62 at three points along the length thereof. The pipes 82 are gas/fluid input-output pipes in fluid communication with the interior of the cylindrical container 62 at each of the three points.

The front end cap 64 is a toroidal disc having a central opening 86. As best seen in FIG. 5, there are four holes 88 around the central opening 86. The four holes 88 receive segments of the four pipes 82 therethrough. The front end cap 64 is welded to the cylindrical container 62 and rotates with the container 62. The outer diameter of the front end cap 64 has gear teeth 84 formed thereon for coupling to a drive for rotating the cylindrical container 62. The rear end cap 66 is also a toroidally shaped disc and it also has gear teeth 92 along its outer diameter for permitting rotation of the cylindrical container 62. The rear end cap 66 is welded to the rear of the cylindrical container 62 and has a central opening 94. The central openings, 86 and 94, allow waste to pass in and out of the chamber 60 as will be more fully described below.

Secured to the front face of the front end cap 64 by pins 95 is a front seal bearing ring 68. The front seal bearing ring 68 is preferably made out of a high strength, resilient, plastic material, such as nylon or a waxy material such as that sold by E. I. Du Pont De Nemours and Company under the trademark TEFLON®. The seal bearing ring 68 rotates with the cylindrical container 62. As shown in FIGS. 5, 6A and 6B, the front seal bearing ring 68 has a central opening 96, an outer rim 98, an inner rim 100, four arcuate channels or inwardly recessed areas 102, wall members or dividers 104 between the recessed areas 102, and four bores or holes 106 penetrating through the thickness of the ring 68. Each arcuate channel or recessed area 102 has one bore or hole 106 and is separated from the adjacent recessed area 102 by a wall member or divider 104. One side of the front seal bearing ring 68 is flat and pinned against the front end cap 64. The four holes 106 in the front seal bearing ring 68 are aligned with the four holes 88 in the front end cap 64 and have the four pipes 82 disposed in them. The central opening 96 of the front seal bearing ring 68 has essentially the same diameter as the central opening 86 of the front end cap 64. Solid waste passes through the central openings, 96 and 86, into or out of the cylindrical container 62.

The rear seal bearing ring 70 has a central opening 108 and is pinned with pins 109 to the rear end cap 66 so it rotates with the cylindrical container 62. The central opening 108 of the rear seal bearing ring 70 has essentially the same diameter as the central opening 94 of the rear end cap 66. Solid waste passes through the openings 108 and 94 out of the cylindrical container 62.

The front and rear seal bearing rings, 68 and 70, are mounted inside counterbores in the front support plate 72 and the back support plate 74. The outer rim 98 of the front seal bearing ring 68 is inserted inside the counterbore 110 (FIG. 4) of the front support plate 72. Inside the counterbore 110 is a central opening 114. The central opening 114 of the front support plate 72 aligns with, and has essentially the same diameter as, the central opening 96 of the front seal bearing ring 68. Waste to be decomposed or reduced passes through the central openings of the front support plate 72, front seal bearing ring 68 and front end cap 64 into the cylindrical container 62. The rear support plate 74 has a counterbore 112 into which the rear seal bearing ring 70 fits. The central opening 116 of the rear support plate 74 is in line with and has essentially the same diameter as the central opening 108 of the rear seal bearing ring 70 and the central opening 94 of the rear end cap 66. The waste in the cylindrical container 62 is discharged from the environmental chamber 60 through the central openings in the rear end cap 66, rear seal bearing ring 70 and the rear support plate 74, as will be further illustrated.

The front support plate 72 and the rear support plate 74 are part of the support frame (not shown) attached to earth. The cylindrical container 62, the front and rear end caps 64 and 66, and the front and rear seal bearings 68 and 70 rotate by virtue of being journaled in the front counterbore 110 of the front support plate 72 and the rear counterbore 112 of the rear support plate 74.

In the counterbore 110 of the front support plate 72 are holes 118 and 120. The holes 118 and 120 in the counterbore 110 of the front support plate 72 align with the circle defined by the recessed areas 102 between the inner rim 100 and outer rim 98 of the front seal bearing 68. The holes 118 and 120 exit the front support plate 72 at its sides, making a 90 degree angle inside the front support plate 72. Fluid and gas pipes are connected to the holes 118 and 120.

As seen in FIGS. 6A and 6B, the front seal bearing ring 68 has an outside rim surface 98, a central opening 96, an inner rim 100 around the central opening 96, and four arcuate channels or recessed areas 102 between the inner rim 100 and the outer rim 98. Four wall members or dividers 104 between the inner rim 100 and the outer rim 98 divide the general recessed area into four distinct arcuate channels or recessed areas 102. The wall members or dividers 104 are at 90° intervals around the front seal bearing ring 68, so that each recessed area 102 extends about one-fourth of the way around the front seal bearing ring 68 between the inner rim 100 and the outer rim 98. Each recessed area 102 also has a bore or hole 106 leading to it. The first hole 118 and the second hole 120 in the front support plate 72 are aligned with the circle described by the recessed areas 102 of the front seal bearing ring 68. Thus, the first hole 118 and the second hole 120 of the front support plate 72 are in fluid communication, through the recessed areas 102 and four holes 106 in the front seal bearing ring 68, the four pipes 82 and the inside of the cylindrical container 62. Fluids and gases are introduced or extracted through the two holes 118 and 120 in the front support plate 72, through the recessed areas 102 of the front seal bearing ring 68 and the four pipes 82, while the environmental chamber 62 rotates. Gases, such as methane, are drawn out through the first hole 118 in the front support plate 72 and fluids and gases needed for decomposition are added through the second hole 120 of the front support plate 72 as chamber rotation continues.

Figure 7:
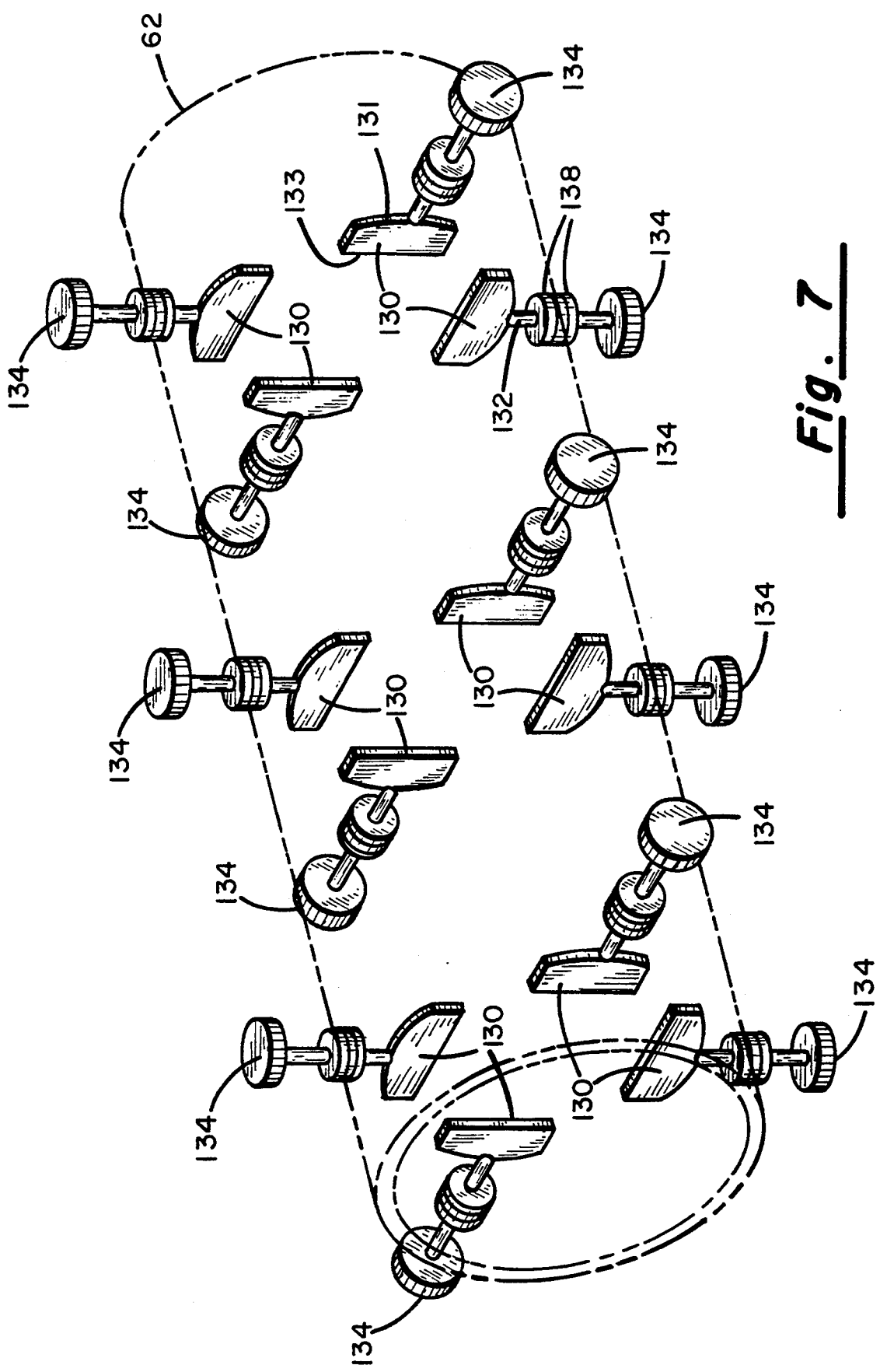
FIG. 7 is a schematic drawing illustrating the directional vane sets relative to the environmental chamber walls.

As shown in FIG. 7, disposed inside the cylindrical container 62 are twelve directional vanes 130. The directional vanes 130 are preferably made out of PVC or steel coated with a waxy material such as that sold by E. I. Du Pont De Nemours and Company under the trademark TEFLON ®. The directional vanes 130 are longitudinally arranged in three sets of four each from the front to the back of the cylindrical container 62. One set of four is located generally proximate the front end, a second set is located generally at the rear end and a third set is located generally in the middle of the cylindrical container 62. Each set of directional vanes 130 is rotationally journaled in a circumferential arrangement around the cylindrical container 62. The four directional vanes 130 comprising a set are disposed at 90° intervals. The directional vanes 130 of one set are horizontally in line with the directional vanes 130 of the other two sets. Each directional vane 130 has an arcuate edge 131 conforming to the interior wall of the chamber 62 and a straight edge 133 facing the center of the cylindrical container 62. The directional vanes 130 do not interfere with one another as they are made to rotate relative to the wall of the chamber.

Figure 8:
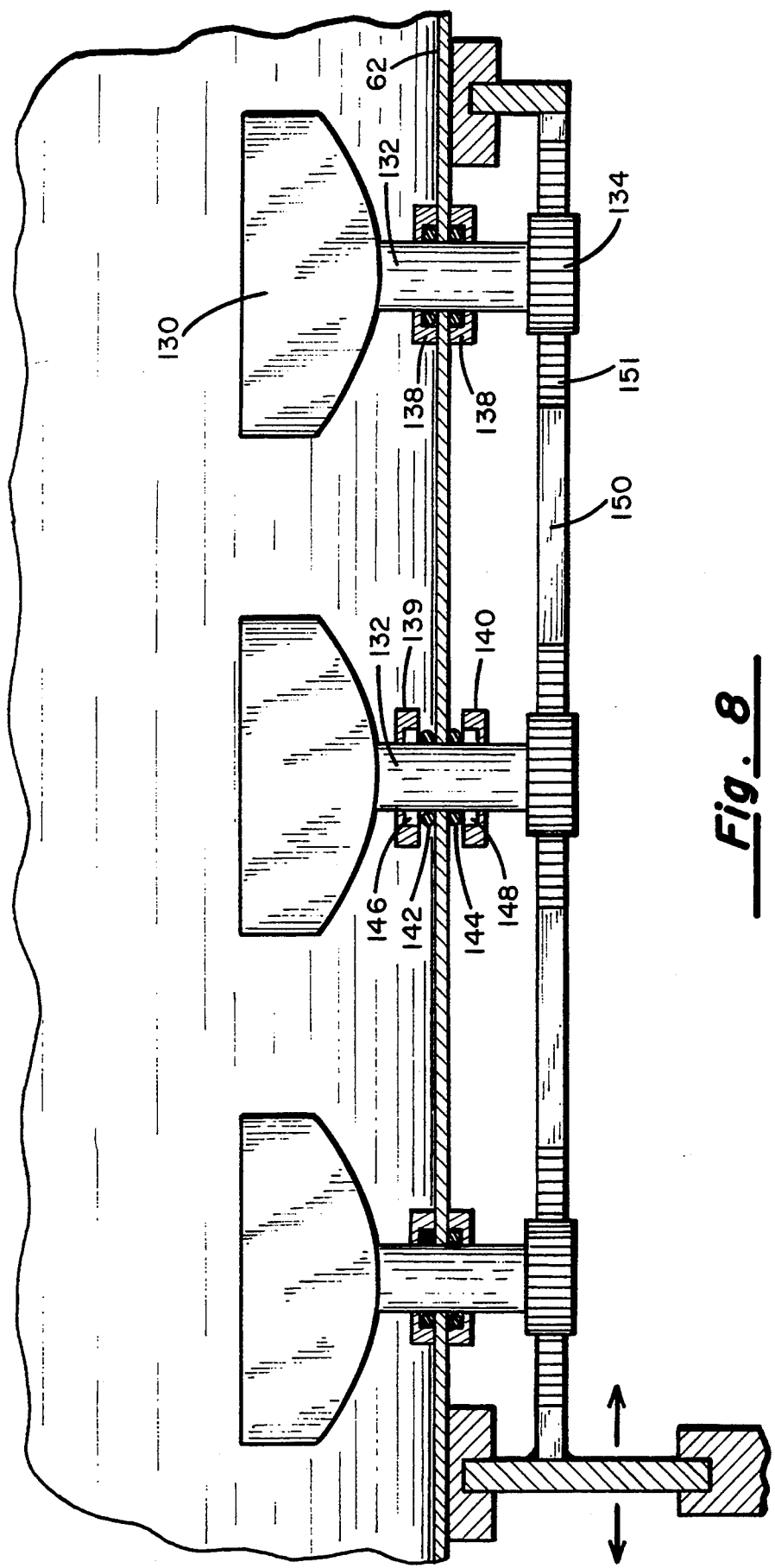
FIG. 8 is a view showing the mechanism for positioning the directional vanes.

As shown in FIGS. 7 and 8, each directional vane 130 is connected to a steel shaft 132 journaled in openings formed through the wall of the chamber 62. A directional vane gear 134 is connected to each shaft 132 on the outside of the container 62. The shaft 132 extends through a seal 138 in the wall of the container 62. The seal comprises an inner seal ring 139, an outer seal ring 140, an inner O-ring 142 and an outer O-ring 144. The inner and outer seal rings 139 and 140 have recessed areas 146 and 148 facing the cylindrical container 62 side wall. The recessed areas 146 and 148 are for surrounding the inner and outer O-rings, 142 and 144. The O-rings are preferably made out of a corrosion resistant rubber or plastic. The inner O-ring 142 fits around the directional vane shaft 132 on the inside of the cylindrical container 62. The inner seal ring 139 fits over the inner O-ring 142 on the directional vane shaft 132 and is securely fastened with bolts to the inside of the cylindrical container 62. Likewise, the outer O-ring 144 fits snugly over the directional vane shaft 132 and the outer seal ring 140 has a recessed area 148 that fits over the top of the outer O-ring 144. The outer seal ring 140 is securely fastened with bolts to the outside of the cylindrical container 62. The directional vanes 130 disposed inside the cylindrical container 62 rotate in the seal 138.

As shown in FIGS. 8 and 9, one of four directional vane gear bars 150, having teeth 151 that mesh with the teeth of the directional vane gears 134, is aligned with three of the directional vane gears 134 disposed at the same 90° interval around the cylindrical container 62. The four directional vane gear bars 150 extend from the front to the rear of the cylindrical container 62 and are attached to circular directional vane gear rings 152 and 154 at the front and the rear of the cylindrical container 62, respectively. The four directional vane gear bars 150 and the two directional vane gear rings 152 and 154 are preferably made out of steel. The front directional vane gear ring 152 and the rear directional vane gear ring 154 are slidably attached to the cylindrical container 62. The slidable connection is achieved using steel slide bars 160 welded to the cylindrical container 62 at 90° intervals around the cylindrical container 62. The slide bars 160 do not interfere with the directional vane gears 134. The directional vane gear rings, 152 and 154, are slidably attached to the bars 160 in a well-known fashion. Thus, the directional vane gear rings, 152 and 154, and the four directional vane gear bars 150, are slidably attached to the cylindrical container 62 and rotate with the cylindrical container 62.

The front directional vane gear ring 152 has a larger diameter than the rear directional vane gear ring 154. The front directional vane gear ring 152 fits between the prongs of a directional fork 164. The directional fork 164 is connected to a motor and a worm gear assembly 166 attached to the frame. The directional fork 164 is moved from left to right longitudinally along the cylindrical container 62 by the motor and worm gear assembly 166 in a conventional fashion. The prongs of the directional fork 164 on each side of the front directional vane gear ring 152 move the front directional vane gear ring 152, the four directional vane gear bars 150, and the rear directional vane gear ring 154 longitudinally. Since the teeth 151 of the four directional vane gear bars 150 are meshed with the twelve directional vane gears 134, the directional vanes 130 disposed inside the cylindrical container 62 rotate reciprocally as the fork 164 is driven back and forth. In this manner, the pitch of the directional vanes 130 are changed in unison while the cylindrical container 62 continues to rotate. By changing the pitch of the directional vanes 130 and speed of rotation of the cylindrical container 62, the mixing and flow of waste in the environmental chamber 60 is regulated.

As seen in FIGS. 4 and 10, the directional vane assembly 80 including the directional vane gear rings 152 and 154 are connected to the cylindrical container 62 inside the front end cap 64 and the rear end cap 66. The four pipes 82 in fluid communication with the inside of the cylindrical container 62 are mounted next to the directional vane gears 134 so as not to interfere with the gears 134. The pipes 82 extend past the front of the cylindrical container 62 and into the front end cap 64, underneath the front directional vane gear ring 152. The front end cap 64 and the rear end cap 66, longitudinally outside the front and rear directional vane gear rings 152 and 154, have gear teeth 84 and 92 that mesh with the gear assemblies 78 for rotating the cylindrical container 62.

As seen in FIGS. 4, 5 and 10, the gear assemblies 78 at the front and rear of the environmental chamber 60 comprise drive gears 170 and 180 and idler gears 172 and 182. The front drive gear 170 is connected to a drive shaft 178 that passes through a hole and bearing 176 in the front support plate. The drive shaft 178 is connected to the motor 76. A tubular extension 174 is connected to the front drive gear 170 and the rear drive gear 180. The rear drive gear 180 is connected to a drive shaft extension 184 that passes through a hole and bearing 186 in the rear support plate 74. The front idler gear 172 is connected to a front idler shaft 188 that fits into a hole and bearing 190 in the front support plate 72. The rear idler gear 182 is connected to a rear idler shaft 192 that fits into a second hole and bearing 194 in the rear support plate 74.

To rotate the container 62, the front idler gear 172 is meshed with the teeth 84 of the front end cap 64 and the rear idler gear 182 is meshed with the teeth 92 of the rear end cap 66. The idler gears 172 and 182 are also meshed with the drive gears 170 and 180. The motor 76 turns the drive shaft 178, the front and rear drive gears 170 and 180, the front and rear idler gears 172 and 182, the front and rear end caps 64 and 66, and the cylindrical container 62.

Figure 11:
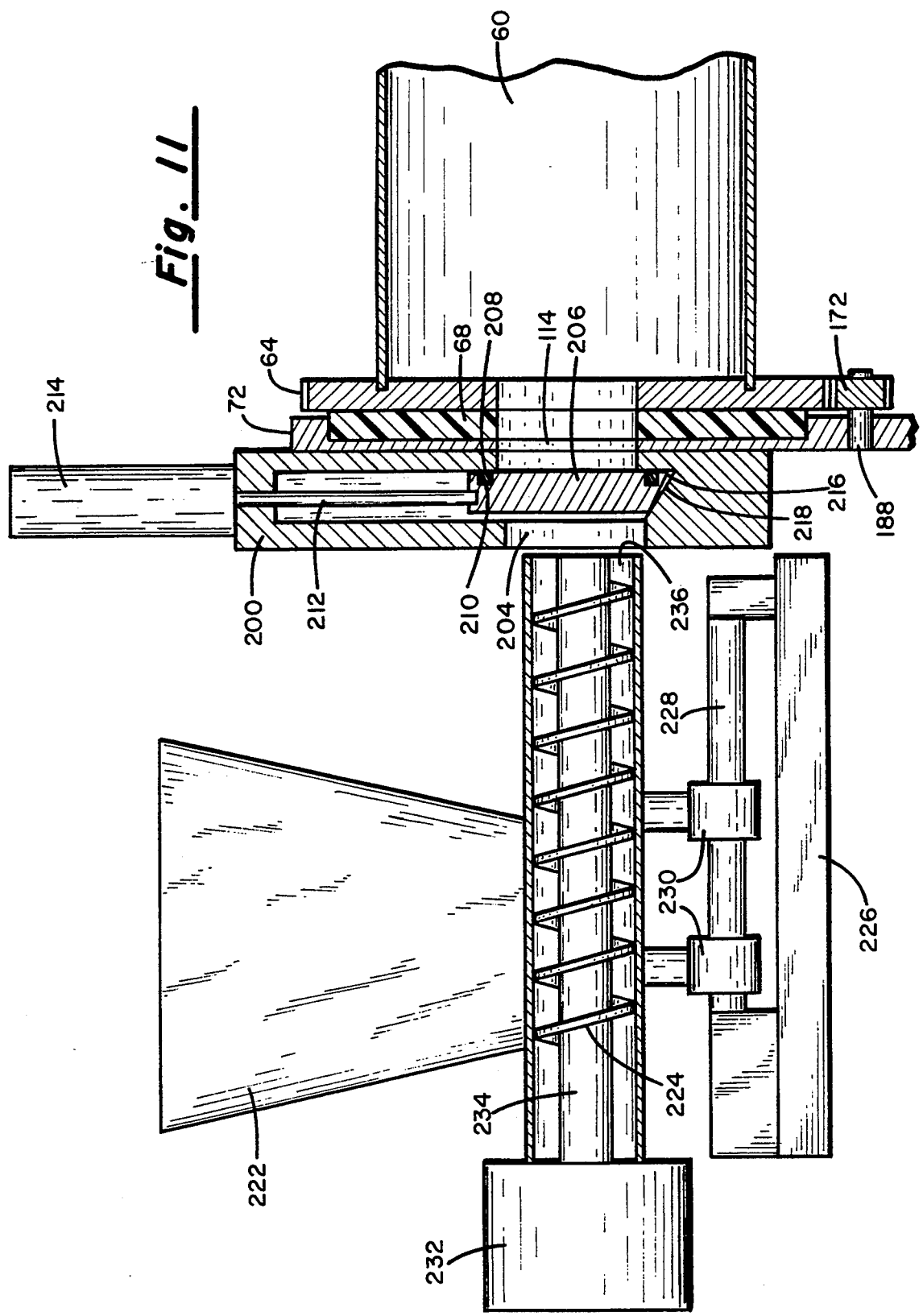
FIG. 11 is a partial cross-sectional view illustrating the input bin and auger with the valve plate of the front isolation valve in the sealed position.

As shown in FIG. 11, a front isolation valve 200 is attached in a well-known manner to the front support plate 72. The front isolation valve 200 is a rectangular box having a central opening 204 passing through its two major surface areas. The central opening 204 is aligned with the central opening 114 of the front support plate 72. The central opening 204 of the front isolation valve 200 is essentially the same in diameter as the central opening 114 of the front support plate 72. Disposed inside the isolation valve 200 is a valve plate 206.

The valve plate 206 is rectangular and large enough to completely cover the central opening 204 of the front isolation valve 200. The valve plate 206 is generally flat having two major surface areas. Set into a circular O-ring groove 210 in one of the major surface areas of the valve plate 206 is an O-ring seal 208. The O-ring seal 208 and O-ring groove 210 are larger in diameter than the central opening 204 of the isolation valve 200.

Figure 13:
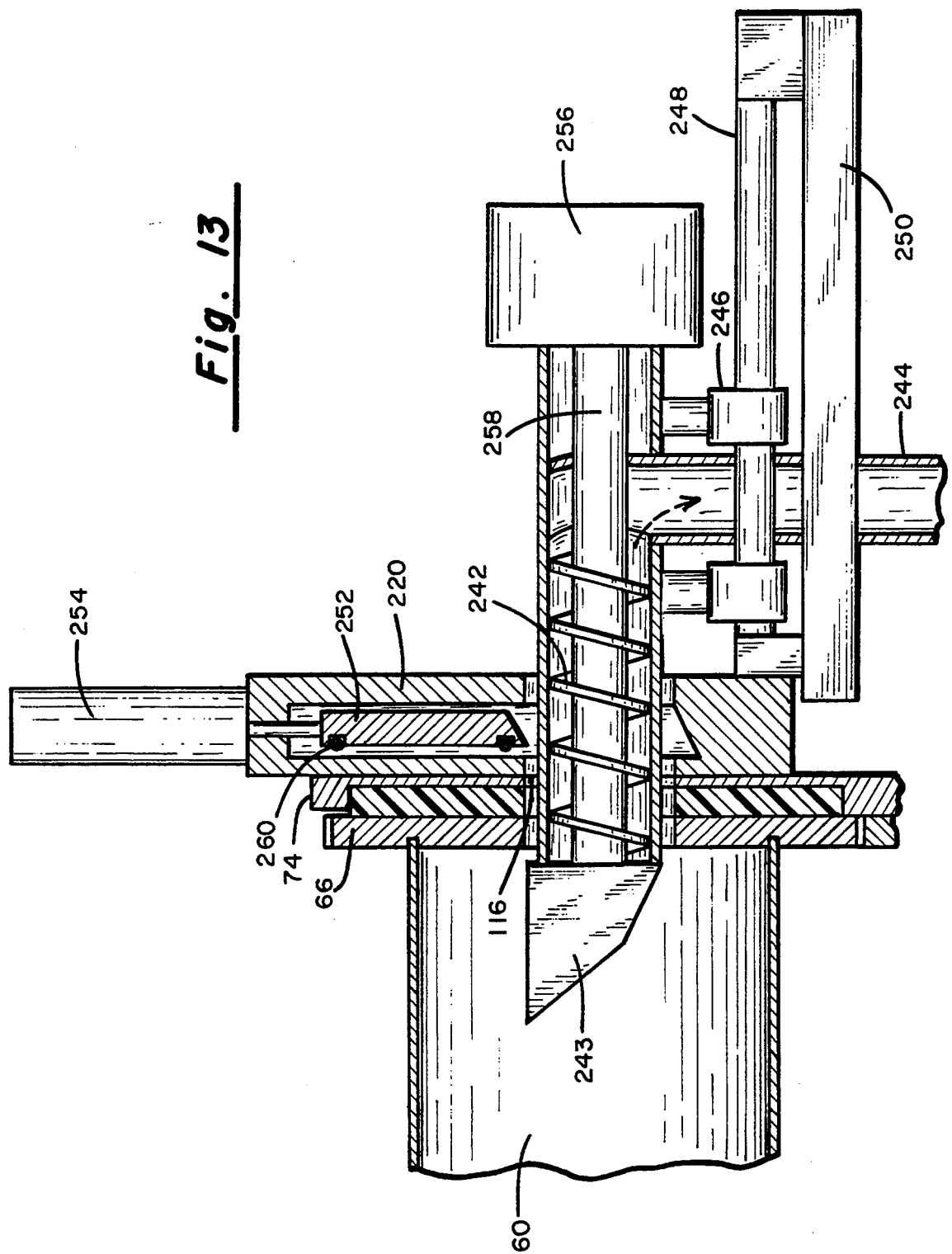
FIG. 13 is a partial cross-sectional view illustrating the output trough, auger and drop chute in position inside the opening of the rear support plate for removing waste as it is discharged from the environmental chamber.

The valve plate 206 is connected to a rod 212 for moving the valve plate 206. The rod 212 passes through the top of the isolation valve 200 into an air driven pump assembly 214 for moving the rod 212 and valve plate 206. The bottom 216 of the valve plate 206 is angled to fit into a complementing angle in the bottom 218 of the inside of the isolation valve 200. As the valve plate 206 is pushed down onto the angled bottom 218 of the isolation valve 200, the complementing angles of the isolation valve 200 and the valve plate 206 guide the valve plate 206 against the inside face of the isolation valve 200. This seals the front of the environmental chamber 60 closed. To close the rear of the environmental chamber 60, a rear isolation valve 220, shown in FIG. 13, is attached in a well-known manner to the rear support plate 74. The rear isolation valve 220 has the same components and functions in the same manner as the front isolation valve 200.

Figure 12:
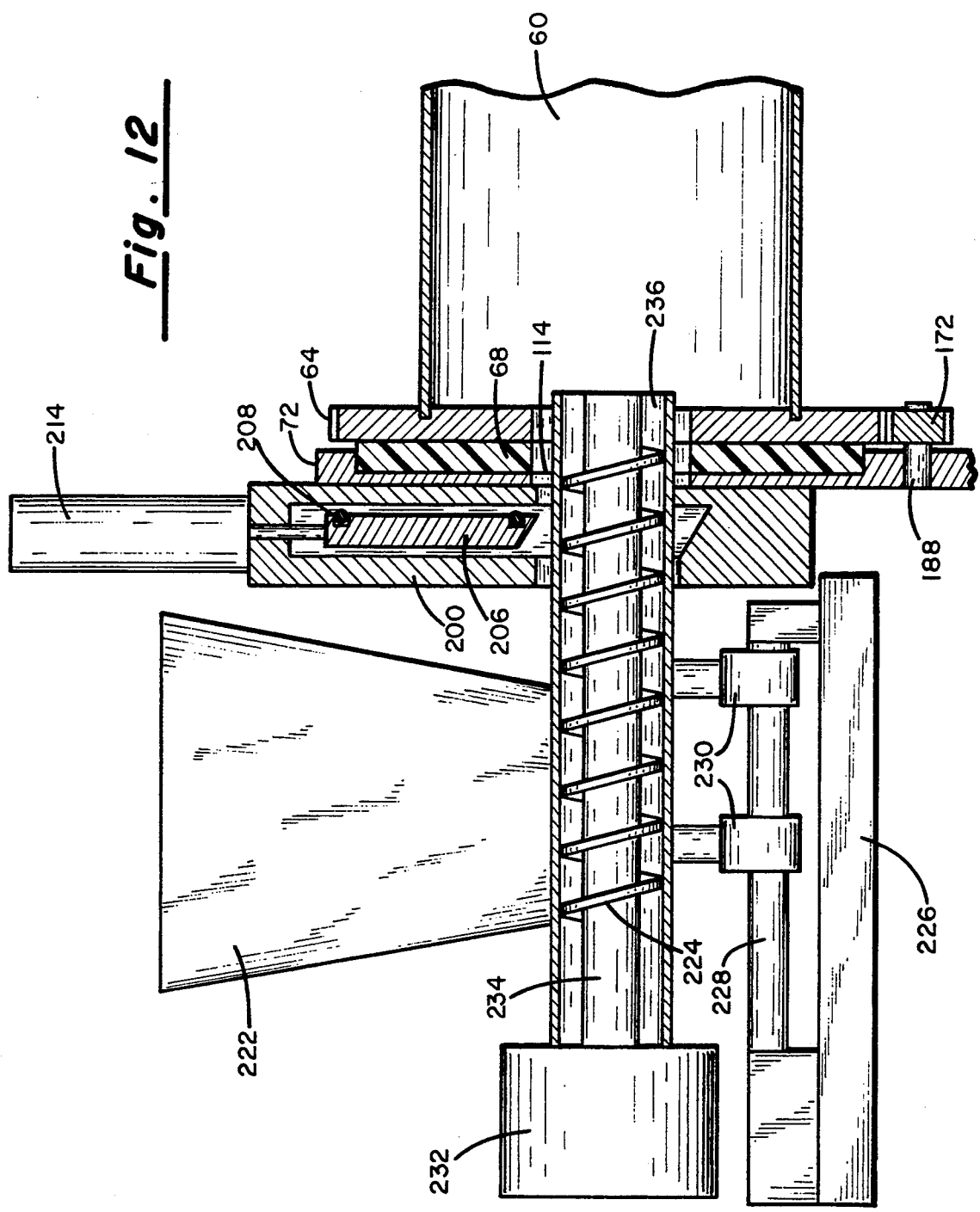
FIG. 12 is a partial cross-sectional view illustrating the input bin and auger in position for transferring waste into the environmental chamber.

As shown in FIGS. 11 and 12, a bin 222 and auger 224 are used to transfer waste into the environmental chamber 60. The bin 222 is attached to the top of the auger 224 and has an opening at its base to allow waste to fall into the auger 224. A motor 232 attached to the shaft 234 of the auger 224 turns the auger 224 so the waste that falls into the auger 224 is pushed to the output or mouth 236 of the auger 224 and into the environmental chamber 60. The bin 222 and auger 224 are attached to an in-out drive assembly 226. The in-out drive assembly 226 has a rail 228 with bearings 230 slidably attached to the rail 228. The bearings are fixedly attached to the auger assembly 224. The bin 222 and auger 224 slide to and from the environmental chamber 60 by the action of a motor and chain in the in-out drive assembly 226.

As shown in FIG. 12, to put waste into the environmental chamber 60, the valve plate 206 is pulled up by the air driven pump assembly 214 and the bin 222 and auger 224 are moved forward on the rails 228 of the in-out drive assembly 226. The output or mouth 236 of the auger 224 fits inside the central opening 114 of the front support plate 72. Waste in the bin 222 drops into the auger 224 and the motor 232 turns the auger 224 forcing the waste into the environmental chamber 60. To seal the front end of the environmental chamber, the bin 222 and auger 224 are moved by the in-out drive assembly 226 and the valve plate 206 is forced down by the air driven pump assembly 214. The O-ring 208 on the valve plate 206 seals the front of the environmental chamber 60 closed.

As shown in FIG. 13, an output trough 243 and auger 242 are used to remove waste from the environmental chamber 60. Waste moved away from the chamber 60 drops through a drop chute 244 and into an awaiting input bin 222 for processing in a subsequent environmental chamber 60. The trough 243, auger 242 and drop chute 244 are connected to rail bearings 246. The rail bearings 246 ride on a rail 248 that is part of a second or rear in-out drive assembly 250. The rear in-out drive assembly 250 moves the trough 243, auger 242 and drop chute 244 to and from the environmental chamber 60.

To remove waste from the environmental chamber 60, the rear isolation valve 220 is opened by lifting the rear valve plate 252 with the rear air driven pump assembly 254. The trough 243 and auger 242 are slid into the central opening 116 of the rear support plate 74 and the pitch of the vanes 130 inside the chamber 60 are changed to push the waste toward the rear support plate 74 and into the trough 243 as the environmental chamber 60 continues to rotate. To increase the rate of discharge of the waste, the speed of rotation of the environmental chamber 60 is increased. Rotating the environmental chamber 60 with the vanes 130 at the correct pitch pushes the waste into the trough 243. The motor 256 attached to the shaft 258 of the auger 242 turns the auger 242 to pull the waste into the drop chute 244. After the desired amount of waste has been removed from the environmental chamber 60, the pitch of the vanes 130 is changed, chamber rotation is decreased and the trough 243, auger 242 and drop chute 244 are slid away from the chamber 60 by a motor and chain inside the rear in-out drive assembly 250. The rear valve plate 252 is lowered by the rear air driven pump assembly 254 forcing the rear O-ring 260 attached to the rear valve plate 252 against the inside surface of the side of the rear isolation valve 220. This seals the rear of the chamber 60 closed.

In operation, a series of chambers 60 are arranged, one before and above the other, to perform the method of decomposing and reducing waste of the invention. Each chamber 60 rotates the entire time. After the solid waste has been prepared and shredded, it is dropped into an input bin 222 and fed into an environmental chamber 60 for anaerobically decomposing the organic waste. The waste is fed into the environmental chamber 60 using the input bin 222 and auger 224. The pH of the waste is measured in a conventional manner and the front of the anaerobic decomposition chamber is sealed. Chemicals for balancing the pH are added through the first and second holes 118 and 120 in the front support plate 72. Heated nitrogen is forced into the waste and air is purged from the inside of the environmental chamber 60 through the same holes, 118 and 120. After enough air has been removed from the environmental chamber 60 and the waste has been heated to the appropriate temperature, up to 180° F., anaerobic bacteria is added to the sealed chamber 60 for anaerobic decomposition. During anaerobic decomposition, nitrogen and methane gas or ethanol are removed from the chamber and separated. The nitrogen is reheated and reused in the sealed chamber 60. The methane gas or ethanol is used as fuel for turbines to generate electricity or sold separately. The electricity is used at the waste disposal plant or sold to public utilities.

After the amount of methane gas or ethanol being produced has slowed to a desired level, the rear valve plate 252 is opened and the trough 243 and auger 242 are moved into the central opening 116 of the rear support plate 74. The pitch of the vanes 130 is changed to push the waste toward the rear support plate 74 and into the trough 243 by moving the directional fork 164 with the motor and worm gear assembly 166. The auger 242 is rotated by the motor 256, and the rotational speed of the chamber 60 is increased, thus discharging the anaerobically decomposed waste from the environmental chamber 60. The output auger 242, rotated by the motor 256, moves the waste to the drop chute 244 and into an awaiting input bin 222.

The awaiting input bin 222 catches the anaerobically decomposed waste for feeding into an environmental chamber 60 for aerobically decomposing the waste. The waste is transferred into an environmental chamber 60 by an auger 224 for aerobic decomposition. The pH of the waste is measured and the environmental chamber is sealed. Chemicals are added for balancing the pH and heated air is added to raise the temperature of the chamber to up to 180° F. Aerobic bacteria is then added to accomplish aerobic decomposition of the waste. After aerobic decomposition is complete, the decomposed waste is transferred from the aerobic decomposition chamber 60 into vibration-grating machines for separating the inorganic waste from the organic waste. This separation process is done at approximately 100° F.

The separated inorganic waste is dropped into an input bin 222 and transferred into an environmental chamber 60 using an auger 224. The input bin 222 and auger 224 are moved away from the environmental chamber 60 and the valve plate 206 is pushed down to seal the chamber 60 shut. The rear valve plate 252 is already sealed shut. A solvent for reducing plastic is injected into the environmental chamber 60 at a temperature just under the solvent's boiling point. The solvent dissolves the desired plastic. Fumes given off during this process are recovered from the environmental chamber, reheated and reused to heat the solvent/waste mixture. After the solvent has had time to dissolve the desired plastic, the solvent is drained through the holes, 118 and 120 in the front support plate 72. The solvent and dissolved plastic are then piped into an evaporator. In the evaporator, the solvent is evaporated and condensed for reuse, leaving the desired plastic material for resale to industry. This process may be repeated as many times as desired in the same environmental chamber 60 or in different environmental chambers for extracting various plastics.

After all plastics have been removed from the inorganic waste, the rear valve plate 252 is opened and a trough 243 and auger 242 are moved into the central opening 116 of the rear support plate 74. The pitch of the vanes 130 in the environmental chamber is changed to push the waste toward the rear support plate 74 and into the trough 243, and the rotational speed of the chamber 60 is increased. The output auger 242, rotated by the motor 256, moves the waste to a drop chute 244 and into an awaiting input bin 222.

An environmental chamber 60 or a series of environmental chambers 60 are used for reducing metals with acids. To reduce metals with acids, the waste is transferred by auger 224 into an environmental chamber 60 through an open front valve plate 206. The rear valve plate 252 is already closed. The front valve plate 206 is then closed to seal the environmental chamber 60 shut. Acids for dissolving various metals are then added and extracted at will to dissolve the metals and recover their basic elements. Hydrogen and oxygen given off during the metals' reduction process are captured and used for generating electricity or sold to industry. The decomposed organic waste is used as a fertilizer supplement and the reduced inorganic plastic and metals are sold for reuse in industry.

This invention has been described herein in considerable detail in order to comply with the Patent Statutes and to provide those skilled in the art with the information needed to apply the novel principles and to construct and use such specialized components as are required. It is to be understood that the invention can be carried out by specifically different means and that various modifications can be accomplished without departing from the scope of the invention itself.

What is claimed is:

1. An apparatus comprising:
    (a) a cylindrical container mounted for rotation about a horizontally disposed longitudinal axis, said cylindrical container having a side wall, a front inlet end and a rear outlet end;
    (b) rotary seal means affixed to said front inlet end for sealing the interior of said cylindrical container from the ambient, said rotary seal means comprising pipe means having a first opening at one end and a plurality of second openings in fluid communication through said side wall of said cylindrical container at longitudinal spaces for introducing and extracting fluids, and further comprising an annular disc having first and second major surfaces and a cylindrical outer diameter, said first major surface having a plurality of arcuate channels formed inwardly therein, each such channel being separated from an adjacent channel by an intermediate wall member, certain channels including a bore extending through said second major surface for receiving said first opening of said pipe means, wherein fluid communication is achieved through said arcuate channels and said bore to said pipe means and the interior of said cylindrical container as said cylindrical container continues to rotate; and
    (c) means contained within said cylindrical container and rotatable from a location exterior to said cylindrical container for controlling the flow of material through said cylindrical container as said cylindrical container continues to rotate.

2. The apparatus as in claim 1 wherein said cylindrical container is supported at said front inlet end by a front support plate having a first annular counterbore, said rotary seal means fitting within said first annular counterbore of said front support plate and acting as a bearing.

3. The apparatus as in claim 2 and further including an annular seal bearing affixed to said cylindrical container at said rear outlet end and a rear support plate having a second annular counterbore, said annular seal bearing disposed within said second annular counterbore in said rear support plate.

4. An apparatus comprising:
    (a) a cylindrical container mounted for rotation about a horizontally disposed longitudinal axis, said cylindrical container having a side wall, a front inlet end and a rear outlet end;
    (b) rotary seal means affixed to said front inlet end for sealing the interior of said cylindrical container from the ambient, said rotary seal means including means for introducing fluids into the interior of said cylindrical container and means for extracting fluids from said cylindrical container as said cylindrical container continues to rotate; and
    (c) vane means inside said cylindrical container for pushing material along said side wall from one end to the other end as said cylindrical container continues to rotate, said vane means connected to a shaft journaled through said side wall of said cylindrical container, said shaft coupled on the exterior of said cylindrical container to means for rotating said vane means to a desired pitch.

5. The apparatus as in claim 4 wherein said means for rotating said vane means to a desired pitch comprises a gear device joined to said shaft, said gear device operatively coupled to a bar connected to a bar ring, said bar ring longitudinally slidable on slide bars.

6. An apparatus comprising:
    (a) a container mounted for rotation along a horizontal longitudinal axis, said container having a side wall, a front end, a rear end, and pipe means for fluid communication with the inside of said container;
    (b) a front support plate having a first major surface area, a second major surface area, and an annular counterbore in said first major surface area, said front support plate having a hole from said annular counterbore to said second major surface area;
    (c) a front seal bearing between said front end and said front support plate, said front seal bearing having a front surface area, a rear surface area and an arcuate channel in said front surface area, said arcuate channel having a hole from said front surface area to said rear surface area, said hole operatively coupled to said pipe means, said arcuate channel in face-to-face relation with said annular counterbore of said front support plate; and
    (d) means at said rear end for supporting said rear end for rotation along said horizontal longitudinal axis.

7. The apparatus of claim 6 further having means for directing the flow of material in said container.

8. The apparatus of claim 7 wherein the means for directing the flow of material in said container is a vane inside said container.

9. The apparatus of claim 8 further having means for rotating said vane.

10. The apparatus of claim 9 wherein said means for rotating said vane comprises:
    (a) a shaft connected to said vane, said shaft extending through said side wall of said container;
    (b) gear means attached to said shaft external to said container; and
    (c) means for rotating said gear means.

11. The apparatus of claim 6 further having means for rotating said container.

12. An apparatus comprising:
    (a) a front support plate having a first annular counterbore;
    (b) a rear support plate having a second annular counterbore;
    (c) a container having a side wall, a front end and a rear end;
    (d) a front rotary seal attached to said front end and a rear rotary seal attached to said rear end, wherein said front rotary seal is inserted in said first annular counterbore and said rear rotary seal is inserted in said second annular counterbore for journaling said container for rotation;
    (e) means for rotating said container; and
    (f) vane means contained inside said container and actuable from a location exterior to said container for pushing material along said side wall from one end to the other end as said cylindrical container continues to rotate, said vane means including a shaft journaled through said side wall of said container.

13. The apparatus as in claim 12 further having gear means attached to said shaft external to said container and means for rotating said gear means.

14. The apparatus as in claim 13 wherein said means for rotating said gear means comprises:
(a) a bar operatively coupled to said gear means, said bar attached to a ring slidably connected to a rail mounted external to said container, said ring capable of sliding longitudinally on said rail; and
(b) means for sliding said ring.

15. The apparatus as in claim 14 wherein the means for sliding said ring comprises a fork having prongs, wherein movement of said fork moves said ring, said bar, and said gear means attached to said shaft of said vane means, thereby rotating said vane means.

16. The apparatus as in claim 12 further having pipe means in fluid communication with the inside of said container.

17. The apparatus as in claim 16 wherein said front support plate is in fluid communication with said pipe means.

18. An apparatus comprising:
(a) a cylindrical container mounted for rotation about a horizontally disposed longitudinal axis, said cylindrical container having a side wall, a front inlet end and rear outlet end;
(b) a pipe having an inlet and a plurality of outlets, said pipe being joined to the exterior of said cylindrical container with said plurality of outlets extending through said side wall of said cylindrical container at longitudinally spaced locations;
(c) rotary seal means affixed to said front inlet end for sealing the interior of said cylindrical container from the ambient, said rotary seal means including an annular disc having first and second major surfaces and a cylindrical outer diameter, said first major surface having a plurality of arcuate channels formed inwardly therein, each such channel being separated from an adjacent channel by an intermediate wall member, certain channels including a bore extending through said second major surface and operatively coupled to said inlet of said pipe, wherein fluid communication is achieved from said arcuate channels through said bore and said pipe into the interior of said cylindrical container; and
(d) means contained within said cylindrical container and actuable from a location exterior to said cylindrical container for controlling the flow of material through said cylindrical container as said cylindrical container continues to rotate.

19. An apparatus comprising:
(a) a cylindrical container mounted for rotation about a horizontally disposed longitudinal axis, said cylindrical container having a side wall, a front inlet end and a rear outlet end;
(b) rotary seal means affixed to said front inlet end for sealing the interior of said cylindrical container from the ambient, said rotary seal means including means for introducing and extracting fluids from said cylindrical container as said cylindrical container continues to rotate; and
(c) vane means contained within said cylindrical container and rotatable from a location exterior to said cylindrical container for pushing material along said side wall from one end to the other end as said cylindrical container continues to rotate, said vane means rotatable to variable pitches.

20. The apparatus as in claim 19 wherein said means for introducing and extracting fluids from said container comprises pipe means having a first open end and a plurality of openings distributed along the length thereof, said pipe means joined to the exterior of said cylindrical container with said plurality of openings extending through said side wall at longitudinally spaced locations, said first opening operatively coupled to said rotary seal means for introducing and extracting fluids from said cylindrical container as said cylindrical container continues to rotate.

21. The apparatus as in claim 20 wherein said rotary seal means comprises an annular disc having first and second major surfaces and a cylindrical outer diameter, said first major surface having a plurality of arcuate channels formed inwardly therein, each such channel being separated from an adjacent channel by an intermediate wall member, certain channels including a bore extending through said second major surface for receiving said first opening, wherein fluid communication is achieved through said arcuate channels and said bore to said pipe means and into the interior of said cylindrical container.

22. The apparatus as in claim 19 wherein said vane means for pushing material along said side wall comprises a vane inside said cylindrical container, said vane connected to a shaft journaled through said side wall of said cylindrical container, said shaft coupled on the exterior of said cylindrical container to means for rotating said vane.

* * * * *